United States Patent [19]

Klugkist et al.

[11] Patent Number: 5,470,561
[45] Date of Patent: Nov. 28, 1995

[54] MOUTHWASH COMPOSITIONS

[75] Inventors: Jan Klugkist, Spital; Charles A. Saxton, Gayton, both of Great Britain

[73] Assignee: Chesebrough-Pond's USA Co., Division of Conopco, Inc., Greenwich, Conn.

[21] Appl. No.: 249,580

[22] Filed: May 26, 1994

Related U.S. Application Data

[63] Continuation of Ser. No. 988,533, Dec. 10, 1992, abandoned.

[30] Foreign Application Priority Data

Dec. 11, 1991 [GB] United Kingdom ............... 9126306

[51] Int. Cl.$^6$ .................................................. A61K 7/16
[52] U.S. Cl. .................................................. 424/49
[58] Field of Search ......................................... 424/49

[56] References Cited

U.S. PATENT DOCUMENTS

| | | | |
|---|---|---|---|
| 4,022,880 | 5/1977 | Vinson et al. | 424/49 |
| 4,132,770 | 1/1979 | Barth | 424/49 |
| 4,824,661 | 4/1989 | Wagner | 424/52 |
| 4,937,066 | 6/1990 | Vlock | 424/52 |
| 4,976,954 | 12/1990 | Kleber et al. | 424/52 |

OTHER PUBLICATIONS

European Search Report in European Patent Application 92203788.2, 1993.
European Search Report in European Application 92203790.8, 1993.
Chemical Abstracts of 140180U, vol. 111, No. 16, Oct. 16, 1989.
Boylan, J. C. "Liquids" *The Theory and Practice of Industrial Pharmacy*, 2nd Ed. 1976, Lea & Febiger, Philadelphia, pp. 541–546.

*Primary Examiner*—Marianne M. Cintins
*Assistant Examiner*—William R. A. Jarvis
*Attorney, Agent, or Firm*—Rimma Mitelman

[57] ABSTRACT

The present invention relates to anti-plaque mouthwash compositions that contain a zinc salt and Triclosan as the anti-plaque system. According to the present invention effective, clear and stable mouthwash compositions with a zinc salt and Triclosan and a humectant system can be obtained with a water level of more than 60% by weight, if the compositions further comprise a surfactant system that comprises a mixture of a nonionic and an anionic surface-active agent.

It is essential that the nonionic surface-active agent should be of the type $H\text{-}(O\text{-}CH_2CH_2)_a\text{-}(O\text{-}CH(CH_3)CH_2)_b\text{-}(O\text{-}CH_2CH_2)_a\text{-}OH$ and should be present in an amount of from 0.5–3% by weight of the composition.

The amount of the anionic surface-active agent in the compositions of the present invention should be such, that the weight ratio of the nonionic to the anionic surfaceactive agent ranges from 4–35, preferably from 5–20.

8 Claims, No Drawings

MOUTHWASH COMPOSITIONS

This is a continuation, of Ser. No. 07/988,533, filed Dec. 10, 1992, now abandoned.

The present invention relates to mouthwash compositions having anti-plaque efficacy. More particularly it relates to anti-plaque mouthwash compositions that contain a zinc salt and Triclosan as the anti-plaque system.

Various mouthwash compositions have been proposed in the art, mainly for the purpose of giving a feeling of freshness in the mouth. Although sometimes also a claim to a certain anti-plaque efficacy is made, nearly none of the mouthwash compositions that are on the market do show any significant anti-plaque benefits. One of the very few products with some anti-plaque benefits is Listerine, a product marketed by Warner Lambert, which consists of a mixture of thymol, hexylresorcinol, menthol, eucalyptol and methylsalicylate in a rather high amount of alcohol; others include Peridex, marketed by Procter and Gamble, and Corsodyl, marketed by ICI, which are based on a solution of chlorhexidine.

Thus, despite the many proposals for mouthwash compositions, only very few that have an anti-plaque benefit have reached the market, and there still exists the need for an effective anti-plaque mouthwash composition.

The combination of a zinc salt and Triclosan is a well-known, effective anti-plaque system, and toothpastes with this anti-plaque system are widely marketed. This system has also been proposed for inclusion in a mouthwash composition, but either the levels thereof are too high for a truly acceptable product, or such compositions suffer from other drawbacks like unpleasant taste, unclear solutions, insufficient storage stability and the like.

In our co-pending UK patent application 9126305.3 of the same date as the present application we have described and claimed that effective, clear mouthwash compositions with a zinc salt and Triclosan can be obtained if the compositions contain a nonionic surface-active agent and contain not more than 60% by weight of water, the compositions further containing a lower aliphatic monohydric alcohol and a humectant.

According to the present invention we have found, that effective, clear and stable mouthwash compositions with a zinc salt and Triclosan and a humectant system can also be obtained with a water level of more than 60% by weight, if the compositions further comprise a surfactant system that comprises a mixture of a nonionic and an anionic surface-active agent.

It has been found that it is essential that the nonionic surface-active agent should be of the type $H\text{-}(O\text{-}CH_2CH_2)_a\text{-}(O\text{-}CH(CH_3)CH_2)_b\text{-}(O\text{-}CH_2CH_2)_a\text{-}OH$ and should be present in an amount of from 0.5–3% by weight of the composition. Furthermore it has been found, that the amount of the anionic surface-active agent in the compositions of the present invention should be such, that the weight ratio of the nonionic to the anionic surface-active agent ranges from 4–35, preferably from 5–20.

Consequently, the present invention relates to aqueous mouthwash compositions which contain a zinc salt and Triclosan as anti-plaque system, a humectant system, and a surfactant system which comprises from 0.5–3% by weight of the composition of a nonionic surface-active agent of the type $H\text{-}(O\text{-}CH_2CH_2)_a\text{-}(O\text{-}CH(CH_3)CH_2)_b\text{-}(O\text{-}CH_2CH_2)_a\text{-}OH$ and an anionic surface-active agent, the latter in an amount such, that the weight ratio of the nonionic to the anionic surface-active agent ranges from 4–35, preferably from 5–20, the amount of water in the compositions being 60% by weight or more. The above features of the present invention are discussed hereunder in more detail.

The zinc salt that is used in the present invention can be any zinc salt that provides an effective amount of $zinc^{2+}$ ions in the oral cavity. Examples of such zinc salts are enumerated in U.S. Pat. No. 4,022,880 and typically suitable zinc salts are zinc phenolsulphonate, zinc sulphate, zinc glycinate, zinc citrate, zinchloride, zinc acetate and so on. They may be used as such, or they may be formed in situ, e.g. zinc glycinate may be formed in situ from zinc sulphate and glycine. Mixtures of various zinc salts may also be used.

The amount of zinc salt used in the composition may vary from 100–4000 ppm, expressed as zinc ions, and will usually range from 200–2000 ppm, preferably from 300–1000 ppm. Triclosan, which is 2',4,4'-trichloro-2-hydroxydiphenyl ether, is used in an amount of 0.01–2%, usually 0.02–0.5% and preferably 0.1–0.3% by weight of the composition.

The humectant system used in the present invention contains sorbitol, and may either consist entirely of sorbitol, or of a mixture of sorbitol with any other well-known humectant, used in the art for oral compositions such as glycerol, propyleneglycol, and polyethyleneglycol. The humectant system is usually used in an amount of 5–30%, preferably 10–25% and especially preferably 10–20% by weight of the composition. Where a mixture of sorbitol with another humectant is used, the amount of sorbitol in that mixture should be at least 25% by weight of the mixture. An example of a suitable mixture is a mixture of sorbitol, glycerol and propyleneglycol.

The nonionic surface-active agent used in the present invention is an ethylene oxide/propylene oxide block copolymer of the general formula

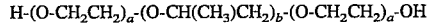

$$H\text{-}(O\text{-}CH_2CH_2)_a\text{-}(O\text{-}CH(CH_3)CH_2)_b\text{-}(O\text{-}CH_2CH_2)_a\text{-}OH$$

in which a and b are integers which are greater than 0, which is commercially available from ICI under the trade name "Synperonic PE" or "Pluronic". Of these block copolymers particularly those, containing 80% by weight of ethylene oxide in the molecule are preferred. Such products have an approximate molecular weight ranging from abt. 4,000 to abt. 15,000, and have an HLB ranging from 27–30.5. Specific examples of these preferred products are Synperonic PE F38, F68, F88 and F108.

The amount of the nonionic surface-active agent, used in the present invention is relatively low and ranges from 0.5–3%, preferably from 0.5–2% and particularly preferably from 0.5–1% by weight of the final composition.

The anionic surface-active agent can be any well-known anionic surface-active agent that is suitable for use in oral products and meets the safety requirements for such use. Typical examples are alkalimetal $C_8\text{-}C_{18}$ alkylsulphates and alkalimetal $C_8\text{-}C_{18}$ alkylbenzenesulphonates, such as for example sodium laurylsulphate and sodium dodecylbenzenesulphonate. Preferred is sodium laurylsulphate.

In general, the amount of the anionic surface-active agent used in the present invention will be fairly low, usually in the order of 0.03–0.3% by weight, particularly 0.05–0.2% by weight of the mouthwash composition. Mixtures of various anionic surface-active agents may also be used.

The water-content of the composition of the present invention must be 60% by weight or more. The water-content may range from 60–90% by weight, preferably from 65–80% by weight. The composition of the present invention may furthermore contain optional other ingredients such as flavours, preferably in an amount of 0.1–0.2%, sweetening agents, colouring agents, polymers, thickening agents, enzymes, other anti-plaque agents, anti-caries agents such as sodium fluoride, anti-tartar agents, anti-sensitive teeth agents etc. The compositions of the present invention furthermore preferably contain a lower aliphatic monohydric alcohol such as ethanol, isopropanol or mixtures thereof, in an amount of 5–25%, preferably 7.5–20% and particularly preferably 10–15% by weight of the composition.

The compositions of the invention should have a pH of between 4 and 8, preferably between 5 and 7, the preferred pH being 6.

The compositions may be in the form of simple liquids, or they may be in the form of gels, suitable for topical application.

The compositions of the present invention can be manufactured by simply mixing the ingredients in any desired or convenient manner. Preferably the order of addition is such that salts which would increase the ionic strength of the solution are added at the final stage.

Thus, a preferred order of addition is first dissolving any flavour and the Triclosan in the aliphatic monohydric alcohol, then adding the surfactants (as solutions), subsequently adding the humectant(s) and finally adding the salts.

The invention will now further be illustrated by way of Example.

EXAMPLE 1

The following formulations were prepared by mixing the various ingredients, the salts being added last.

|  | % by weight | | | |
| --- | --- | --- | --- | --- |
|  | A | B | C | Placebo |
| Triclosan | 0.15 | 0.15 | 0.15 | — |
| Zinc sulphate heptahydrate | 0.40 | 0.40 | 0.40 | — |
| Glycine | — | 0.50 | 0.50 | — |
| Ethanol | 10.0 | 7.5 | 7.5 | 6.0 |
| Sorbitol (70% syrup but calculated as 100% active material) | 17.5 | 14.0 | 4.9 | 5.6 |
| Glycerol | — | — | 9.0 | 4.0 |
| Propyleneglycol | — | — | 4.0 | — |
| Cremophor RH 40 | — | — | — | 0.09 |
| Synperonic PE F68 | 1.0 | 0.5 | 0.5 | — |
| Sodium laurylsulphate | 0.03 | 0.10 | 0.10 | — |
| Flavour | 0.1 | 0.15 | 0.15 | 0.1 |
| Sodium fluoride | 0.02 | 0.02 | 0.02 | 0.0553 |
| Colouring agent | 0.003 | 0.003 | 0.003 | 0.003 |
| Sodium saccharinate | present | present | present | present |
| Water | 70.847 | 76.797 | 72.897 | 83.9 |

The pH was adjusted with NAOH to 6. (products B and C) and 6.25 (placebo).

These products A–C were first tested for clarity and storage stability. For that purpose they were stored at room temperature for a period of three months, after which they were visually assessed whether they were clear and whether a sediment had formed.

All these formulations were found to be clear, without any sediment formed, after the three months' storage period.

These products were also tested as to their anti-plaque efficacy. For that purpose the plaque growth inhibition (PGI) was determined as follows:

The effectiveness of the mouthwash compositions of this invention in inhibiting the growth of plaque on the teeth was determined by following a standard procedure for the measurement of plaque growth. The methodology of measuring plaque growth is that according to Harrap as described in J. Clin. Periodontol., 1974, 1, 166–174 which gives a procedure for assessing the amount of plaque on the teeth adjacent to the gingival margin. The procedure is as follows:

During the late afternoon each subject brushes his/her teeth with a simple, non-active toothpaste (placebo) (having a composition as given hereinafter) for an unspecified period of time to remove as much plaque as possible. This is immediately followed by rinsing with water. Subsequently, any remaining plaque is disclosed by applying an aqueous solution of Erythrosin (0.5% w/w) to the teeth using a soft camel hair brush. Excess dye is removed by rinsing with water and the amount of plaque assessed and recorded for each of 16 teeth (numbers 3 to 6 for each quadrant). The recorded plaque is designated $P_0$. Thereafter, the mouth is rinsed for one minute with 10 ml of the mouthwash to be tested.

No further oral hygiene is permitted for 18 hours after which time each subject rinses his/her mouth with water to remove food debris and viscous saliva. Plaque assessment is then carried out as before and recorded ($P_{18}$). The values of $P_{18}$ and $P_0$ for each tooth are averaged to give a $P_{18}$ and $P_0$ value per mouth. The mean of the values obtained for the subjects in the test is the plaque growth value. Panels of at least 12 subjects are used with each subject using each of the mouth washes in a randomised block sequence. The plaque growth value for a product without active ingredients is usually in the range 22 to 26. The plaque growth inhibition (PGI) is then computed for each test treatment by expressing the percentage inhibition compared to placebo:

$$PGI = \frac{PG_{pl} - PG_T}{PG_{pl}} \times 100\%$$

wherein $PG_{pl}$=recorded plaque of the placebo and $PG_T$= recorded plaque of the test composition.

The composition of the simple, non-active toothpaste referred to above was the following:

| Ingredient | % |
| --- | --- |
| Alumina trihydrate | 50.00 |
| Glycerin | 27.00 |
| Hydroxyethylcellulose | 0.95 |
| Titanium dioxide | 0.50 |
| Water to | 100.00 |

Compositions A–C were assessed as to their PGI in accordance with the above test protocol, and were found to have the following PGI values:

| A | B | C |
| --- | --- | --- |
| 29% | 27% | 26% |

EXAMPLE 2

For comparison purposes, the following mouthwash composition were prepared:

|  | % by weight | |
|---|---|---|
|  | D | E |
| Triclosan | 0.03 | 0.15 |
| Zinc phenolsulphonate octahydrate | 0.70 | — |
| Zinc sulphate heptahydrate | — | 0.20 |
| Glycine | — | 0.5 |
| Ethanol | 7.8 | 6.0 |
| Sorbitol (70% syrup) | 7.8 | 7.0 |
| Glycerol | 16.3 | — |
| Propylene glycol | 7.4 | — |
| Gantrez -S 97* | 0.25 | — |
| Cremophor RH 40* | — | 1.0 |
| Sodium laurylsulphate | 0.4 | 0.34 |
| Sodium lauroylsarcosinate | 0.2 | — |
| Flavour | 0.2 | 0.2 |
| Water (including water stemming from the sorbitol syrup) | 61.22 | 86.7 |

*Gantrez -S 97 is a vinylmethylether/maleic anhydride copolymer ex GAF.
*Cremophor RH is a hydrogenated castor oil, condensed with 40 moles of ethylene oxide, commercially available from BASF.

The storage stability test showed, that products D and E were clear but their PGI values were 21% and 18% respectively.

EXAMPLE 3

The following formulations were made:

| Ingredient | Concentration (w/w %) | | | | |
|---|---|---|---|---|---|
|  | A | B | C | D | E |
| Triclosan | 0.15 | 0.15 | 0.15 | 0.15 | 0.15 |
| ZnSO4 heptahydrate | 0.4 | 0.4 | 0.4 | 0.4 | 0.4 |
| Flavour | 0.1 | 0.1 | 0.1 | 0.1 | 0.1 |
| Ethanol | 10.0 | 10.0 | 10.0 | 10.0 | 10.0 |
| Sorbitol (as 100%) | 17.5 | 17.5 | 17.5 | 17.5 | 17.5 |
| Synperonic F68 | 1.0 | 1.0 | 1.0 | 1.0 | 1.0 |
| Sodium lauryl sulphate | 0.00 | 0.01 | 0.02 | 0.03 | 0.05 |
| water | 70.85 | 70.84 | 70.83 | 70.82 | 70.80 |
| ratio nonionic:anionic | — | 100 | 50 | 33.3 | 20 |
| APPEARANCE |  |  |  |  |  |
| at 4° C. | cloudy | cloudy | cloudy | clear | clear |
| at 20° C. | clear | clear | clear | clear | clear |

These results show that products with a nonionic/anionic ratio outside the ranges of the invention are not satisfactorily clear.

EXAMPLE 4

The following formulations were made: Ingredient Concentration (w/w %)

| Ingredient | Concentration (w/w %) | | | | |
|---|---|---|---|---|---|
|  | A | B | C | D | E |
| Triclosan | 0.15 | 0.15 | 0.15 | 0.15 | 0.15 |
| ZnSO4 heptahydrate | 0.4 | 0.4 | 0.4 | 0.4 | 0.4 |
| Glycine | 0.5 | 0.5 | 0.5 | 0.5 | 0.5 |
| Flavour | 0.15 | 0.15 | 0.15 | 0.15 | 0.15 |
| Ethanol | 7.5 | 7.5 | 7.5 | 7.5 | 7.5 |
| Sorbitol (as 100%) | 14.0 | 14.0 | 14.0 | 14.0 | 14.0 |
| Synperonic F68 | 1.0 | 1.0 | 1.0 | 1.0 | 1.0 |
| Sodium lauryl sulphate | 0.00 | 0.05 | 0.1 | 0.15 | 0.2 |
| water | 76.3 | 76.25 | 76.2 | 76.15 | 76.1 |
| ratio nonionic/anionic | — | 20 | 10 | 6.6 | 5 |
| APPEARANCE |  |  |  |  |  |
| at 4° C. | cloudy | clear | clear | clear | clear |
| at 20° C. | cloudy | clear | clear | clear | clear |

These results show that according to the present invention clear products are obtained.

EXAMPLE 5

The following formulations were prepared: Ingredient Concentration (w/w %)

| Ingredient | Concentration (w/w %) | | | | | |
|---|---|---|---|---|---|---|
|  | A | B | C | D | E | F |
| Triclosan | 0.15 | 0.15 | 0.15 | 0.15 | 0.15 | 0.15 |
| ZnSO4 heptahydrate | 0.4 | 0.4 | 0.4 | 0.4 | 0.4 | 0.4 |
| Glycine | 0.5 | 0.5 | 0.5 | 0.5 | 0.5 | 0.5 |
| Flavour | 0.15 | 0.15 | 0.15 | 0.15 | 0.15 | 0.15 |
| Ethanol | 7.5 | 7.5 | 7.5 | 7.5 | 7.5 | 7.5 |
| Sorbitol (as 100%) | 14.0 | 14.0 | 14.0 | 14.0 | 14.0 | 14.0 |
| Synperonic F68 | 0.00 | 0.20 | 0.40 | 0.50 | 0.60 | 1.00 |
| Sodium lauryl sulphate | 0.1 | 0.1 | 0.1 | 0.1 | 0.1 | 0.1 |
| water | 77.2 | 77.0 | 76.8 | 76.7 | 76.6 | 76.3 |
| ratio nonionic:anionic | — | 2 | 4 | 5 | 6 | 10 |
| APPEARANCE |  |  |  |  |  |  |
| at 4° C. | cloudy | cloudy | cloudy | clear | clear | clear |
| at 20° C | cloudy | cloudy | cloudy | clear | clear | clear |

These results show that the minimum amount of nonionic surface-active agent should be 0.5% to obtain clear products.

EXAMPLE 6

The following products were made, further illustrating the invention:

| Ingredient | Concentration (w/w %) | | | |
|---|---|---|---|---|
|  | A | B | C | D |
| Triclosan | 0.15 | 0.15 | 0.15 | 0.15 |
| ZnSO4 heptahydrate | 0.4 | 0.4 | 0.4 | 0.4 |
| Glycine | 0.5 | 0.5 | 0.5 | 0.5 |
| Flavour | 0.15 | 0.15 | 0.15 | 0.15 |
| Ethanol | 7.5 | 7.5 | 7.5 | 7.5 |

-continued

|  | Concentration (w/w %) | | | |
| --- | --- | --- | --- | --- |
| Ingredient | A | B | C | D |
| Sorbitol (as 100%) | 3.5 | 7.0 | 10.5 | 14.0 |
| Synperonic F68 | 0.5 | 0.5 | 0.5 | 0.5 |
| Sodium lauryl sulphate | 0.1 | 0.1 | 0.1 | 0.1 |
| water | 87 | 84 | 80 | 77 |
| APPEARANCE | | | | |
| at 4° C. | clear | clear | clear | clear |
| at 20° C. | clear | clear | clear | clear |

EXAMPLE 7

The following formulations were made, to further illustrate the invention:

|  | Concentration (w/w %) | | |
| --- | --- | --- | --- |
| Ingredient | A | B | C |
| Triclosan | 0.15 | 0.15 | 0.15 |
| ZnSO4 heptahydrate | 0.4 | 0.4 | 0.4 |
| Glycine | 0.5 | 0.5 | 0.5 |
| Flavour | 0.15 | 0.15 | 0.15 |
| Ethanol | 7.5 | 7.5 | 7.5 |
| Sorbitol (as 100%) | 7 | 4.9 | 4.9 |
| Glycerol | 5 | 5 | 9 |
| Propyleneglycol | 5 | 4 | 4 |
| Synperonic F68 | 0.5 | 0.5 | 0.5 |
| Sodium lauryl sulphate | 0.1 | 0.1 | 0.1 |
| water | 74 | 77 | 73 |
| APPEARANCE | | | |
| at 4° C. | clear | clear | clear |
| at 20° C. | clear | clear | clear |

EXAMPLE 8

The following mouthwash compositions were prepared:

|  | % by weight | | | | |
| --- | --- | --- | --- | --- | --- |
|  | A | B | C | D | placebo |
| Triclosan | 0.15 | 0.15 | 0.15 | 0.15 | — |
| Zinc sulphate heptahydrate | 0.40 | 0.40 | 0.40 | 0.40 | — |
| Glycine | 0.50 | 1.00 | 0.50 | 0.50 | — |
| Ethanol | 7.50 | 10.00 | 6.00 | 7.50 | 6.00 |
| Sorbitol (70% syrup) | 20.00 | — | 7.00 | 20.00 | 8.00 |
| Glycerol | — | 10.00 | — | — | 4.00 |
| Cremophor RH40 | — | 1.00 | 1.00 | — | 0.09 |
| Synperonic PE/F68 | 0.50 | — | — | — | — |
| Synperonic PE/F108 | — | — | — | 1.50 | — |
| Sodium laurylsulphate | 0.10 | — | 0.34 | — | — |
| Flavour | 0.15 | 0.20 | 0.20 | 0.15 | 0.10 |
| Sodium fluoride | 0.02 | 0.02 | 0.02 | 0.02 | 0.0553 |
| Colouring agent | 0.0003 | 0.0005 | 0.0005 | 0.0003 | 0.003 |
| Sodium saccharinate | — | — | 0.04 | — | present |
| Water | 70.68 | 77.23 | 84.35 | 69.78 | 81.8 |

For all formulations the pH was adjusted with NaOH to 6. These formulations were submitted to the PGI-test as described in Example 1, using the above-identified placebo, and the following results were obtained:

| Product | PGI-value |
| --- | --- |
| A | 21% |
| B | −2% |
| C | 14% |
| D | 12% |

Product A, which is according to the present invention, was found to be significantly superior to products B–D, which are not according to the present invention.

We claim:

1. An aqueous mouthwash composition comprising from 100–4000 ppm, expressed as zinc ions, of a zinc salt and from 0.01–2% by weight of 2',4,4'-trichloro-2-hydroxy diphenyl ether as antiplaque system, from 5–30% by weight of a humectant system which comprises sorbitol, and a surfactant system, wherein the surfactant system comprises from 0.5–3% by weight of the composition of a nonionic surface-active agent of the ethyleneoxide/propylene oxide block copolymer type $H\text{-}(O\text{-}CH_2\text{-}CH_2)_a\text{-}(O\text{-}CH(CH_3)CH_2)\text{-}(O\text{-}CH_2CH_2)_a\text{-}OH$ in which a and b are integers, greater than 0, said nonionic agent having an approximate molecular weight of about 4,000 to about 15,000 and having an HLB-value of between 27 and 30.5, and a anionic surface-active agent selected from the group consisting of alkalimetal $C_8\text{-}C_{18}$ alkylsulphates, alkalimetal $C_8\text{-}C_{18}$ alkylbenzene sulphonates, and mixtures thereof, the weight ratio of the nonionic surface-active agent to the anionic surface-active agent ranging from 4 to 35, the amount of water in the composition being at least 60% by weight of the composition, said mouthwash having both clarity and an effective plaque growth inhibition value.

2. The composition according to claim 1, wherein the nonionic surface-active agent contains about 80% by weight of ethylene oxide in the molecule.

3. The composition according to claim 1, wherein the weight ratio of the nonionic surface-active agent to the anionic surface-active agent ranges from 5 to 20.

4. The composition according to claim 1, wherein the anionic surface-active agent is sodium laurylsulphate.

5. The composition according to claim 1, containing from 65–80% by weight of water.

6. The composition according to claim 1, wherein the humectant system comprises a mixture of sorbitol and another humectant selected from the group consisting of glycerol, propyleneglycol, polyethyleneglycol and mixtures thereof, the amount of sorbitol being at least 25% by weight of the mixture.

7. A composition according to claim 1, further comprising from 5–25% by weight of a lower aliphatic monohydric alcohol.

8. The composition according to claim 1, wherein the zinc salt is zinc glycinate or zinc phenol sulphonate.

* * * * *